(12) United States Patent
Ongaro et al.

(10) Patent No.: US 8,142,732 B2
(45) Date of Patent: Mar. 27, 2012

(54) AUTOCLAVE WITH SHORTENABLE WORK CYCLE, CONTAINER TO BE EMPLOYED THEREWITH AND FULL STERILISATION TREATMENT EMPLOYING SAID CONTAINER

(75) Inventors: Daniele Ongaro, Villa di Serio (IT); Renzo Vedovelli, Brusaporto (IT); Ruediger Range, Milan (IT)

(73) Assignee: W & H Sterilization S.r.l., Brusaporto (Bergamo) (IT)

( * ) Notice: Subject to any disclaimer, the term of this patent is extended or adjusted under 35 U.S.C. 154(b) by 938 days.

(21) Appl. No.: 11/817,981

(22) PCT Filed: Mar. 7, 2006

(86) PCT No.: PCT/IB2006/050703
§ 371 (c)(1), (2), (4) Date: Sep. 7, 2007

(87) PCT Pub. No.: WO2006/126103
PCT Pub. Date: Nov. 30, 2006

(65) Prior Publication Data
US 2008/0193337 A1     Aug. 14, 2008

(30) Foreign Application Priority Data
Mar. 7, 2005   (IT) ............... MI2005A0349

(51) Int. Cl.
*A61L 2/08* (2006.01)
*A61L 2/00* (2006.01)
*A61L 9/00* (2006.01)
*B08B 3/00* (2006.01)

(52) U.S. Cl. ............... 422/305; 422/1; 422/26; 422/28; 422/295; 422/298; 422/300; 422/307; 134/95.2; 134/95.3; 134/170; 134/171; 134/297

(58) Field of Classification Search ............ 422/1, 26, 422/28, 295, 298, 300, 305, 307; 134/95.2, 134/95.3, 170–171, 297
See application file for complete search history.

(56) References Cited

U.S. PATENT DOCUMENTS
5,543,119 A    8/1996  Sutter et al.
6,251,345 B1   6/2001  Palmers
2004/0062693 A1 * 4/2004 Lin et al. ............. 422/297

FOREIGN PATENT DOCUMENTS
WO   WO 00 59552     10/2000
WO   WO 00/59552   * 10/2000
WO   WO 00/59553   * 10/2000

* cited by examiner

*Primary Examiner* — Jill Warden
*Assistant Examiner* — Monzer Chorbaji
(74) *Attorney, Agent, or Firm* — Young & Thompson

(57) ABSTRACT

An autoclave for the sterilization of clinical dental instruments is described, of the type comprising a sterilization chamber (1) equipped with a series of appliance fittings (4) for the inflow and outflow of fluids, and apt to contain a load of instruments onto which to carry through a sterilization cycle, characterized in that said appliance fittings (4) are gathered on at least one connection body or partition (3), with which a reducing container (7) is quickly able to be engaged and disengaged, which container has a volume apt to contain at least one instrument to be sterilized, the inner volume of such container (7) communicating with said appliance fittings (4) and said container (7) being apt to be entirely contained within said sterilization chamber (1). The small-volume container for said autoclave is further described, as well as a full treatment system employing said container.

13 Claims, 9 Drawing Sheets

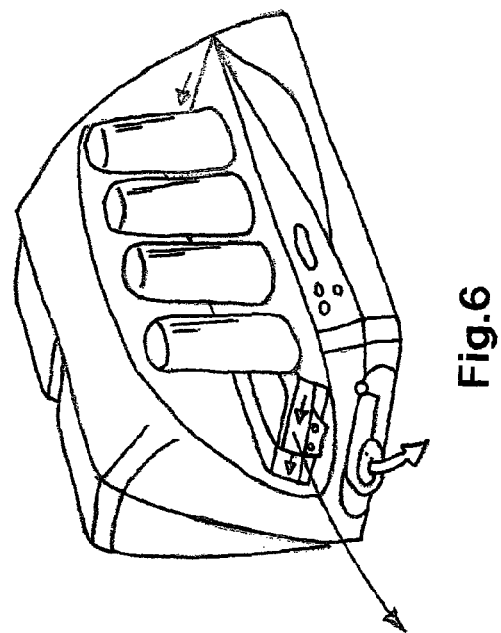
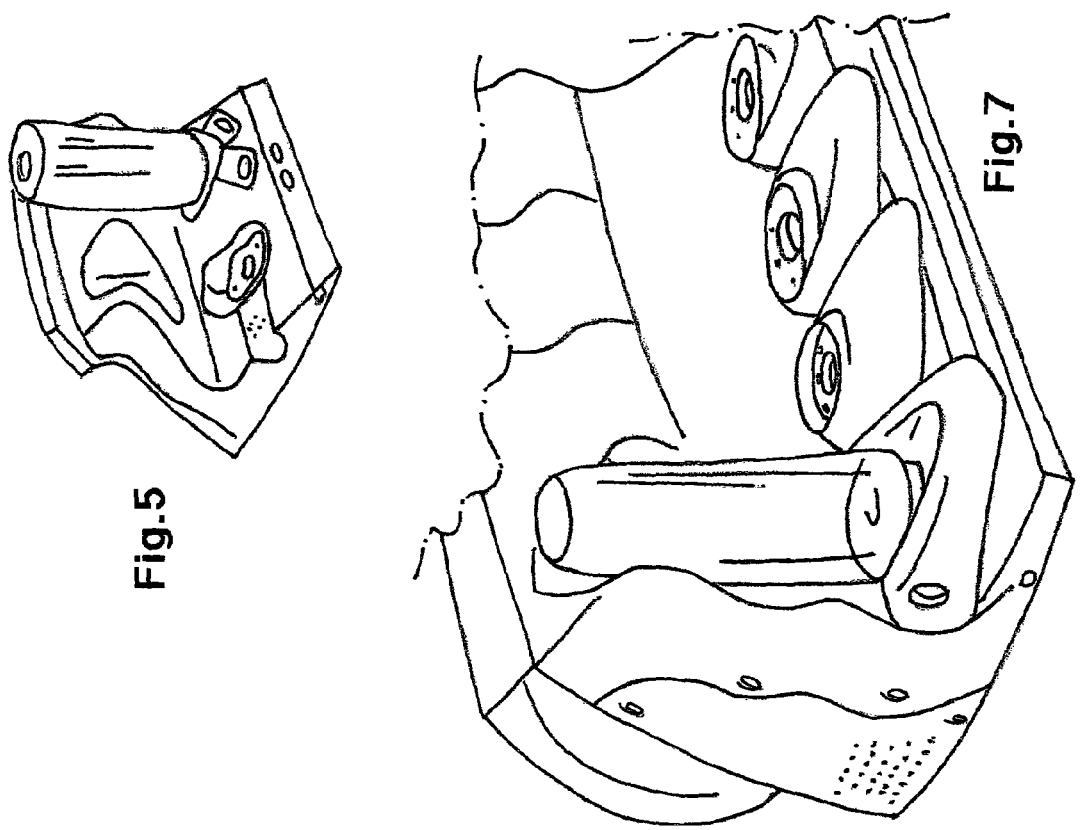

Master

AUTOCLAVE WITH SHORTENABLE WORK CYCLE, CONTAINER TO BE EMPLOYED THEREWITH AND FULL STERILISATION TREATMENT EMPLOYING SAID CONTAINER

BACKGROUND OF THE INVENTION

1. Field of the Invention

The present invention relates to an autoclave for the sterilisation of medical instruments, for example for dental use. In particular, the invention relates to an improved autoclave, as well as to an equipment and arrangement suitable to shorten the work cycle thereof and which can also be employed in a surgery system for the full treatment of medical instruments.

2. Description of the Related Art

In doctor's surgeries, in particular dental surgeries, the use of small-sized autoclaves to sterilise small manual instruments or dental handpieces is well-known. In this context, it is to be borne in mind that by the term "dental handpieces", counterangles and turbines are meant, that is, dynamic devices which comprise hollow and/or porous bodies into which various driving members are placed in rotation.

A known exemplary autoclave is disclosed for example in EP 992.247, which is hereby incorporated by reference.

The autoclaves most widely used in doctor's surgeries usually have a sterilisation chamber with a volume in the order of 15-25 liters. The chamber is equipped with suitable racks or baskets for the insertion of small trays or object-holding drawers. The trays—about 4 or 5 thereof—provide an overall bolster capable of simultaneously housing a variety of objects to be sterilised: therefore, all the medical equipment used during the course of a working day or of half a working day, can be sterilised together during unproductive clinical time (for example during lunch break or in the evening). In this way, the temporary unavailability of the instruments and devices in the autoclave—for the time required for completion of the sterilisation cycle, about 40-70 minutes—does not represent a limitation to the availability thereof during the doctor's clinical time.

However, concentrating treatment operations of dental handpieces and turbines—comprising one or more of the washing, maintenance, disinfection, cold sterilization, sterilisation, drying and lubricating processes—into one or two events during the day, means that a large number of these instruments must be available, even bearing in mind the ever growing trend to treat turbines and handpieces after each use on a patient: this implies a large financial investment, considering the high cost of turbines and handpieces, which is certainly unwelcome to the dental doctor.

Therefore, in small surgeries or in special circumstances (for example when sterilisation of a series of instruments between patients is required) the time of unavailability of the instruments being treated in the autoclave represents an undesired constraint.

In order to overcome this drawback, since for example sterilisation must in any case comply with minimum times of exposure to the sterilising agent, an effective way to cut down operation time is to act on evacuation times—which evacuation encompasses alternating steps of positive-pressure and negative-pressure impulses—of the sterilisation chamber, which evacuation occurs repeatedly during the same "fractionated vacuum" sterilisation cycle, and on drying times.

At present only two alternatives to reduce such times have been suggested: one provides to increase the power of the vacuum pump and of the steam generator, whereas the other provides to adopt a smaller-volume sterilisation chamber.

In the former case, however, a high purchasing cost of the components and of the corresponding power consumption is in any case to be borne by the user, even though for most of the working conditions, longer sterilisation times are tolerable.

In the latter case, instead, the autoclave is offered on the market with a sterilisation chamber which is remarkably smaller than standard ones (for example the 5.5-liter Millennium Bi model manufactured by Mocom, or the 5-liter 13-B or 14-B Vacuquick® model manufactured by Melag) and at a slightly lower price, but the drawback lies in the fact that, in order to manage heavier-than-scheduled workloads, the user is forced to run the sterilisation process very frequently, with a particularly poor power yield.

Both these solutions consequently have drawbacks, but, most importantly, they do not allow versatile and efficient utilisation of the autoclave to manage both light and medium-heavy workloads.

Moreover, additional problems exist with the handling of dental handpieces. Handpieces in fact also require maintenance, such as deep cleaning, lubrication and drying. To carry out these additional operations, the market currently offers various specific appliances (see, for example, Assistina™ manufactured by W&H, Care3™ by Nsk Nakanishi Inc., QuattroCare™ by Kavo), capable of performing cleaning, lubrication and drying quickly and effectively. However, they imply additional costs and require room in the dentist's surgery. Besides, the instrument always requires manual transfer from the maintenance appliance to the autoclave and vice-versa—possibly after being sealed in a blister pack—which does not contribute to a fully sterile cleaning cycle.

On the other hand, more complex appliances (see, for example, DACUniversal™ by Nitram) also exist, which are capable of performing a full treatment cycle (i.e. comprising cleaning, lubrication and sterilisation). However, these appliances are currently rather complex and bulky, since they are designed to treat multiple instruments at the same time (for example six turbines), and they still have some technical problems, such as humidity persistence in the handpieces (which negatively affect storage), as well as long cooling down times, which keep the instruments from being available to clinicians within a short period of time. Finally, it must be noted that at the end of the treatment the instruments still need to be manually removed, thereby affecting sterility thereof. Basically, these devices are capable of performing treatments of multiple instruments only for immediate use thereof, with no opportunity for storage (conservation) and/or transportation of such instruments.

SUMMARY OF THE INVENTION

It is hence an object of the present invention to overcome the drawbacks set forth above by providing a system which, despite resorting to a standard-sized autoclave (in terms of chamber volume and pump power), allows to shorten the sterilisation cycle only when desired, with a low cost and without resorting to permanent capacity changes. At the same time it is intended to provide a full sterilisation system which is also more flexible and capable of performing other maintenance treatments, too.

According to a first aspect of the invention, an autoclave is provided for the sterilisation of dental instruments, of the type comprising a sterilisation chamber, equipped with a series of operative fittings for fluid inflow and outflow, apt to contain a load onto which to carry through a sterilisation cycle, wherein said operative fittings or inlets/outlets are gathered on a connection body whereto a small-sized container apt to contain at least one instrument to be sterilised may be quickly fitted and unfitted, the inner volume of said container communicating with said operative fittings and said container being shaped so as to tightly engage with said connection body, to be fully enclosable in said sterilisation chamber and being capable of withstanding treatment stresses.

According to another aspect of the invention, a small-volume, self-contained sterilisation container capable of withstanding treatment stresses (temperature, negative and positive relative pressure, steam and other treatment agents) is provided, which can be connected either to a sterilising appliance or to other cleaning and lubricating appliances, between which it can be transferred keeping the inner environment thereof unchanged and isolated from the outside.

According to a further aspect of the invention, a full cleaning, lubricating and sterilising system is provided employing a single appliance base capable of accommodating a plurality of small-sized self-contained containers, wherein full treatment of medical instruments occurs without the need to expose such instruments to the outer environment.

Other inventive aspects of the autoclave are described in the dependent claims.

BRIEF DESCRIPTION OF THE DRAWING FIGURES

Further features and advantages of the invention will in any case become clearer from the following detailed description, given by way of example and illustrated in the accompanying drawings, wherein:

FIGS. 5-7 are diagrammatical perspective views of some embodiments of functional base units onto which self-contained containers are applicable according to the invention in a stand-alone version;

DETAILED DESCRIPTION OF THE INVENTION

Figure 1:
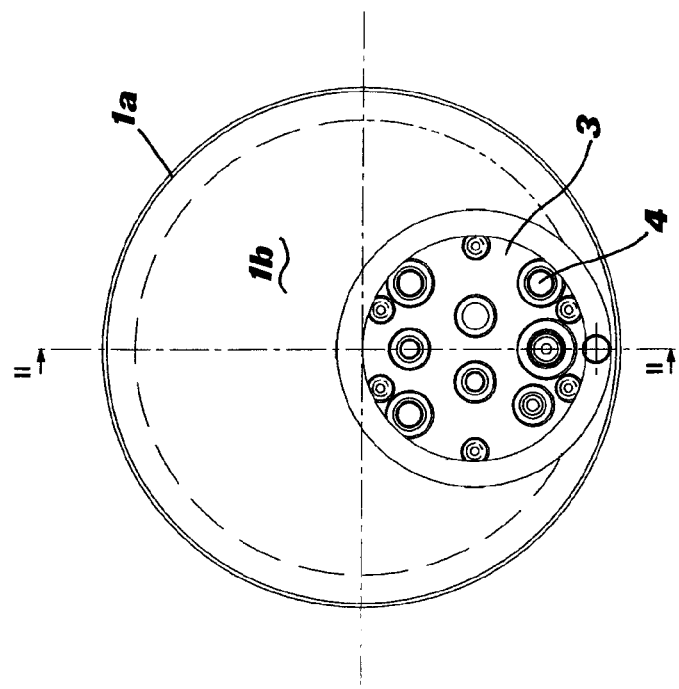
FIG. 1 is an elevation front view of a sterilisation chamber according to the invention.
Figure 2:
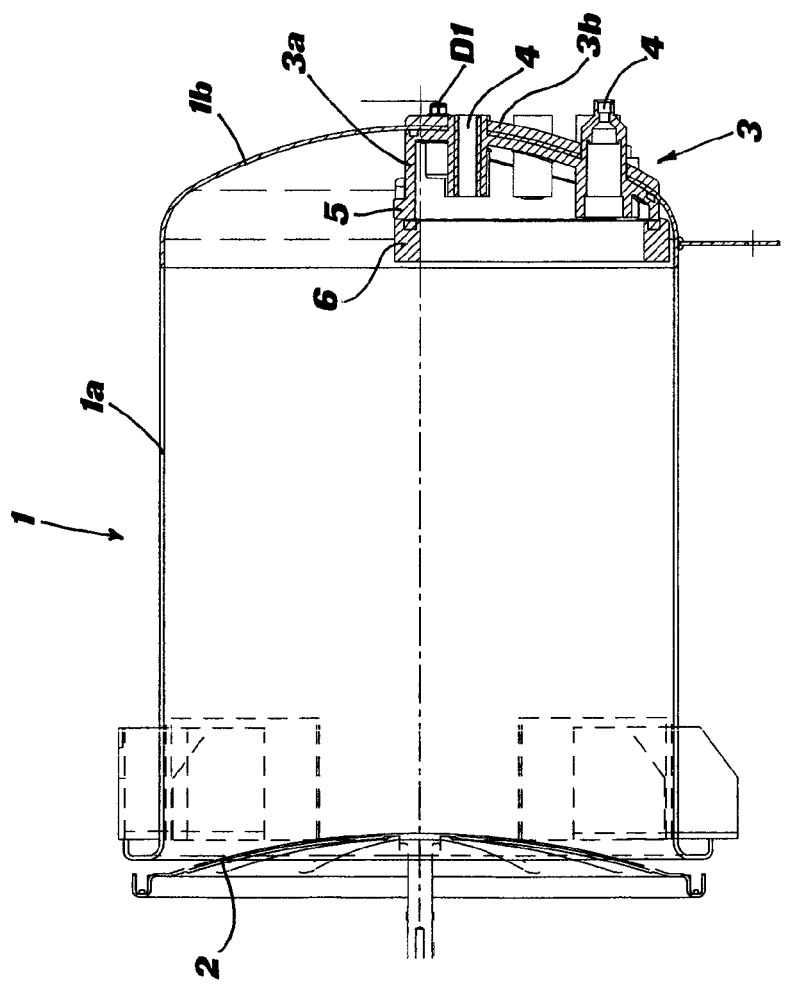
FIG. 2 is a longitudinal section view taken along the line II-II of FIG. 1.

FIGS. 1 and 2 diagrammatically show a sterilisation chamber of an autoclave, defined by a casing 1 and by an air-tight door 2. Typically, casing 1 and door 2 are made of stainless steel, of a thickness apt to withstand a pressure difference of about −1÷2.5 atm between chamber inside and outside. In any case, the chamber can also be made of other materials, such as aluminium or polymeric plastic materials.

The casing 1 for example has a volume of 17 liters and can run a standard class-B sterilisation cycle on a 4.5-kg load with an available power of 2100 Watt over about 40 minutes (Lisa® MB17 model manufactured by W&H Sterilization Srl).

The chamber traditionally consists of a main tubular part 1a and of a spherical bottom plate 1b.

Moreover, according to the known art, a series of holes are bored in the bottom of base plate 1b, to which holes connection tubes are welded for the various fittings (discharge, steam inlet, vacuum pump suction, and so on) required for the operation of the sterilization chamber.

According to the invention, instead, on the base plate 1b of chamber 1 a single wide aperture of a suitable size is bored—for example of a diameter about half the diameter of the chamber—wherein a connection or partition body 3 is applied and secured.

In particular, as can be seen in the section of FIG. 2, connection body 3 consists of an inner piece 3a and of an outer piece 3b, which can be coupled together by interposing sealing means, so as to abut on the two opposite sides of base plate 1b, also enclosing part of the aperture edge. The two inner and outer pieces 3a and 3b, respectively, are then pack-fastened to each other through fastening means, such as a series of six nuts D1 onto circumferentially arranged stud bolts D2.

Figure 3:
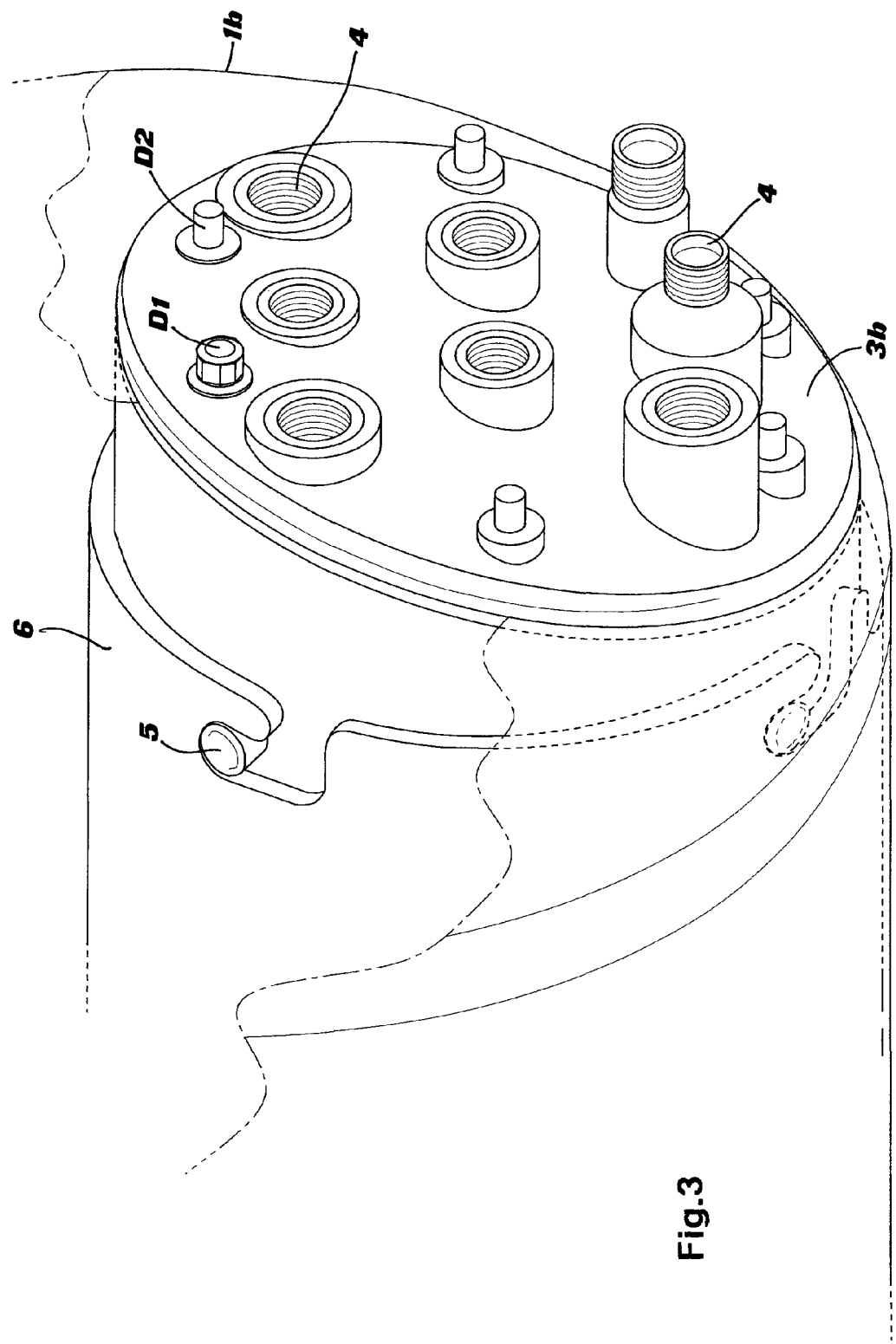
FIG. 3 is a perspective cut-off view of the connection body of the autoclave according to the invention.

A certain number of connection channels 4 is provided on this connection body 3, which channels can be integrally moulded therewith, for example with inner piece 3a. The connection channels 4 are intended to house a corresponding number of inlets or outlets of appliance fittings or of specific sensors (see FIG. 3). The two pieces 3a and 3b of the connection body are made for example of a synthetic material such as 30% glass-filled polyetherimide (Ultem® 2300 available from General Electric Company).

This solution alone already implies a significant cost reduction over the prior art in that it allows to avoid the numerous and expensive welds on base plate 1b of chamber 1.

The connection body 3 may preferably comprise a deflector wall or flap means (not shown) provided on the inner side of inner piece 3a. This flap means is apt to deflect any gas or steam flow coming from the inlets and entering the chamber, so that it does not impinge directly on to the load placed in the chamber.

Figure 4:
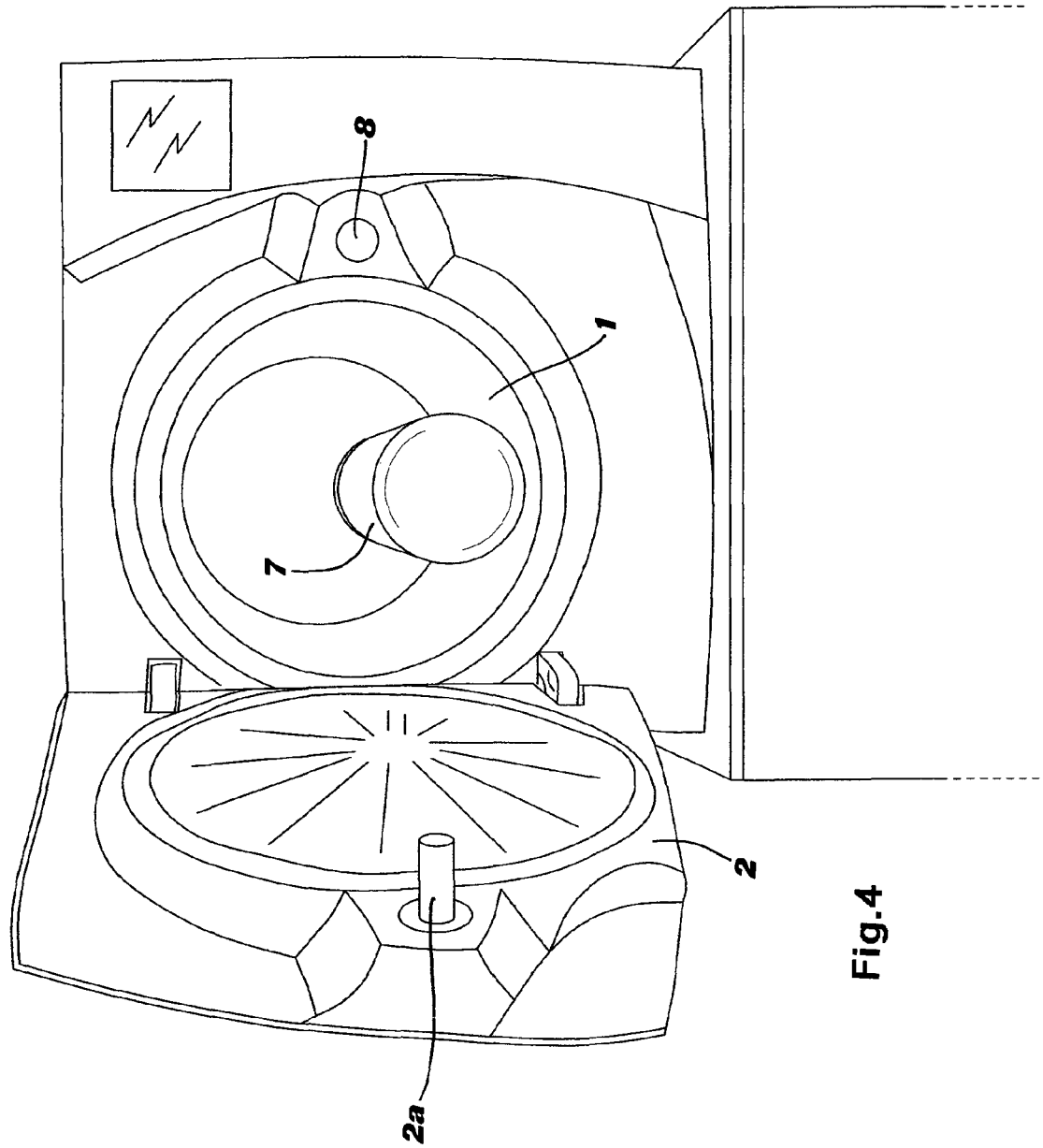
FIG. 4 is a perspective view of the front side of an autoclave according to the invention, complete with the reducing container connected.

Moreover, according to the invention, inner piece 3a comprises a series of connecting means, for example shaped as retaining studs 5, apt to hold—through bayonet engagement—a ring nut or flange 6 of a can-shaped reducing container 7 (FIG. 4). The connecting means can of course be of a different type, too, which the skilled person will be able to identify also according to his preference.

The can-shaped container 7 is substantially a self-contained, small-volume (for example less than 2/3 of the autoclave chamber) pot for containing handpieces and other dental instruments. It has a shape and a thickness so as to suitably withstand the pressures, the temperatures and other agents typical of the treatment cycle, in particular of the sterilisation cycle. Typically, it can be in the shape of a cylinder or of a 3D ellipse generally open at a mouth end.

In the context of the present specification, "self-contained" means that container 7 can autonomously withstand pressurisation, by being engaged with partition body 3, without the need of other enclosing or strengthening means cooperating with the surface thereof.

A particularly preferred material for the container is a glass-filled polymer, particularly glass-filled polyetherimide, which has insulating and sturdiness properties particularly suitable for the use described.

Reducing container 7, through ring 6 and connecting means 5, is sealingly fitted to connection body 3 so as to substantially form a small sterilisation and/or treatment chamber, into which all operative fittings 4 converge, which are required to complete a sterilisation cycle and also, possibly, a cleaning, lubrication, drying cycle.

Thus, thanks to the provision of connection body 3 and to the quick-fit means for reducing container 7, it is possible to temporarily obtain a substantially smaller sterilisation chamber, wherein—thanks to the reduced volume—it is possible to achieve quick evacuation and drying and, in the final analysis, a short sterilisation cycle, for example of 10-15 minutes and a full treatment lasting 15-20 minutes.

Advantageously, thanks to the reduced dimensions of the sterilisation compartment defined by reducing container 7 (for example 280-300 mm long and with a 120-130 mm diameter), the stresses to which its structure is subject are certainly smaller than those of a conventional sterilisation chamber: this allows to use polymeric materials which offer a number of advantages, including thermal insulating properties, which increase efficiency of the work cycle and make for easier and more immediate manipulation of reducing container 7 by an operator.

If desired, reducing container 7 can be equipped with holding elements, such as a handle, by which it can be easily engaged with and freed off connection body 3, without having to introduce one's hand into chamber 1, thereby avoiding the risk of accidental hand contact with the hot walls of pot 1.

According to a variant, reducing container 7 is shaped so as to be apt to be opened also from the opposite end to the mouth end connecting it with partition body 3. This variant is convenient when the dentist does not want to each time disengage container 7 from partition 3, but prefers to use container 7 simply as a fixed smaller chamber. In such case, the handle also serves the function of acting on and sealing an end door (not shown) of container 7. Such door can be hinged along one side thereof, or it can be completely detachable from the main body of container 7; in any case, between the door and the remaining portion a seal should preferably be provided.

Partition 3 can be advantageously equipped with detection systems—for example microswitches—of the correct fitting of container 7—which allow to inhibit autoclave operation until effective and proper engagement has been achieved.

Since, according to this embodiment, reducing container 7 is fully housed within original chamber 1 of the autoclave, user protection from unexpected implosions or explosions can in any case be provided by door 2 of the autoclave. This allows to loosen design constraints of the reducing container itself.

According to a preferred mode of operation, during operation of the autoclave with reducing container 7 inserted, door 2 is not hermetically closed, so that expansions/shrinkage of the air volume within chamber 1 can be released through the gap between chamber 1 and door 2. For such purpose, it is sufficient to provide for retaining element 2a of door 2 to be able to be locked in its seat 8 in an intermediate position, which leaves door 2 slightly a jar with respect to the opening rim of chamber 1.

For example, in W&H's model Lisa®, which already provides progressive tightening of door 2 through electric operation, it is sufficient to provide intermediate stop of the electric control.

This specific mode of operation also allows to immediately detect any leakage in reducing container 7 (for example between the door and the main body in the lockable version of the container, or due to seal damage or formation of microcracks in the thickness of the material): during operation of the vacuum pump, in fact, it would not be possible to reach the desired condition of underpressure (vacuum) within an expected time, because there would be a continuous inflow of air from the outside environment through the door, which could be easily detected and used to signal an anomalous condition to the user.

For the remainder, autoclave operation with reducing container 7 inserted—into which the instruments to be sterilised have been loaded beforehand—is fully equivalent to the one of the autoclave without the reducing container, and will hence not be reported here in detail because it is well-known to skilled people in the field.

According to a preferred embodiment, reducing container 7 also has, at the mouth opening of ring nut 6, a porous membrane or other similar closing means, through which a work fluid can be introduced and flushed out (for example air, steam, and so on), to complete the sterilisation cycle, but which allows to keep the inner environment of container 7 sterile even after having detached the reducing container from partition 3. In this case, advantageously, reducing container 7 does not only serve as a small-volume treatment and sterilisation chamber, but also as a real storage container where to leave sterilised and dried instruments before use thereof on a patient.

The sealing membrane is, for example, a membrane having micropores which are permeable to fluids and to treatment agents, but which are impermeable to contaminating bacteria, such as a membrane made of foamed PTFE (for example, GORE™ Medical Membrane available from W. L. Gore & Associates, Inc.).

This solution further allows to avoid the classic final packaging step, i.e. inserting the instruments to be sterilised in the blister or air-tight, bacteria-proof pack, with the further advantage of removing any contaminating handling of the instruments. The various reducing containers, containing even a single instrument, can hence be stored individually, to be opened later when use of the instrument stored therein is required. For such purpose the reducing containers can be labelled, to clearly identify their contents, or they can be provided with a see-through cut-out entirely manufactured of a clear polymeric material (for example Duran®, available from SCHOTT Duran Produktions GmbH & Co. KG, or Pyrex™) or glass, which allows to glimpse the contents.

According to another preferred embodiment, on connection body 3 there are provided not only appliance fittings to perform sterilisation, but also specific appliance fittings to perform cleaning, disinfecting, cold sterilization and—only in the case of dynamic instruments—lubrication and air-drying as well. For example, the connection body has an injection head of the type shown in EP 1.430.851 and, inside the autoclave casing, devices suitable to carry through a cleaning and lubrication cycle are arranged, such as reservoirs for detergent and lubricant, compressed-air ducts, injection pump, and so on. Alternatively, the injection head is arranged integrally with the reducing container 7, in particular with a wall closing the end at which ring nut 6 is provided, and a corresponding quick-fit connection into partition 3 is provided accordingly.

Figure 8:
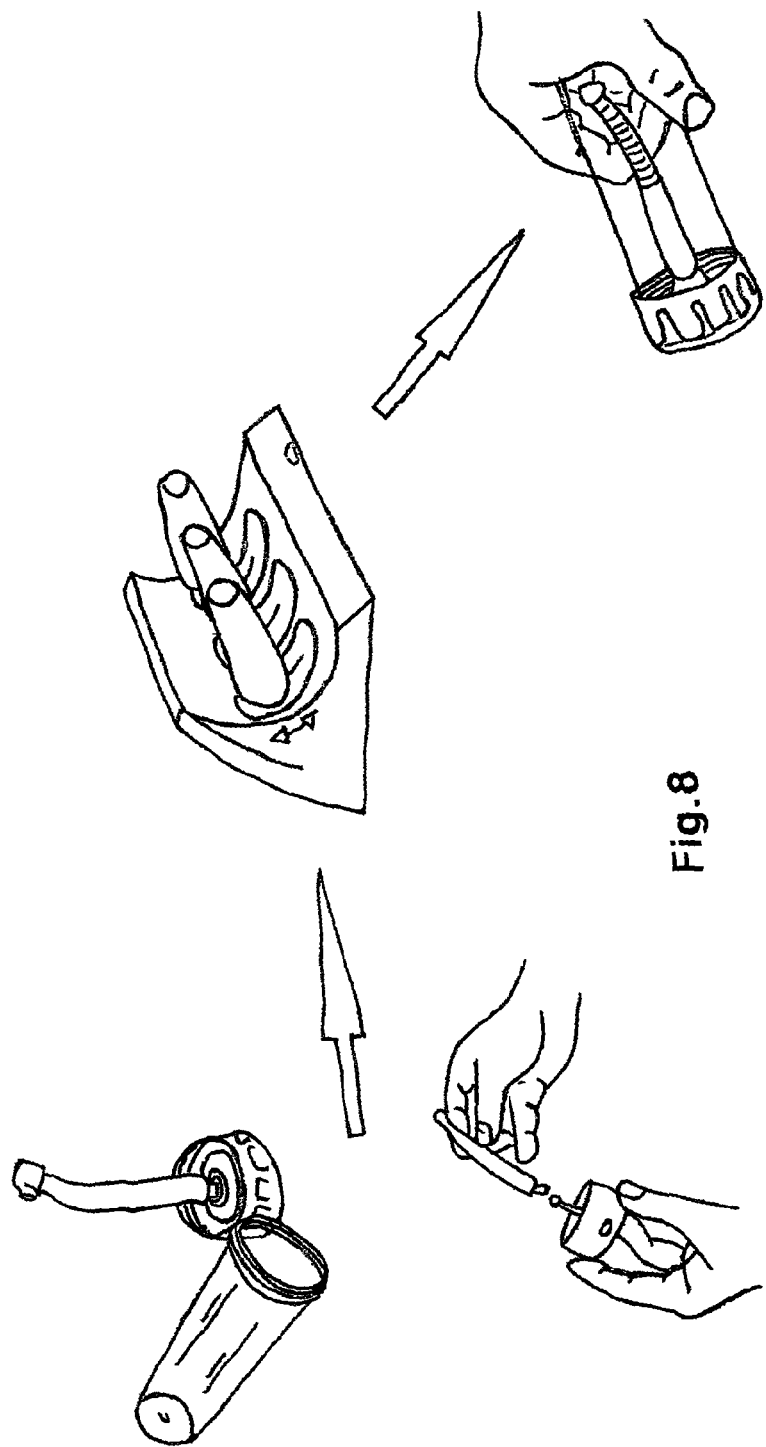
FIG. 8 is a diagrammatical view showing a way of treatment of a self-contained container according to the invention.

In that respect, FIG. 8 shows a possible mode of use of such a small-sized container 7, combined with a particular embodiment of the sterilisation system which will be described in greater detail below.

Should the injection head be provided integral with reducing container 7, as shown in FIG. 8, said reducing container may also be provided to be used as a carrier to transfer the handpiece from one appliance to another—for example connecting it first to a maintenance device and then to an autoclave—with the enormous advantage of not having to directly touch the handpiece.

This mode allows to employ conventional treatment appliances. In case the reducing container is itself equipped with a universal fitting, by which handpieces are conventionally joined to treatment machines, it would be apt to replace the "naked" handpiece and could be fixed to conventional machines (possibly partly adapted) for handpiece cleaning and lubrication.

In any case, according to this embodiment, the opportunity is provided to empty the liquid and gaseous contents of the reducing container 7 before sterilisation, either by using the same vacuum intake of an autoclave or by arranging a specific appliance fitting 4 capable of sucking at least conditioning liquids such as cleaning and lubrication ones from within the reducing container.

Preferably, a liquid evacuation outlet arranged on the autoclave is shaped so as to have a downward bend (with respect to the operational reference plane of the autoclave), so as to arrange a suction port in close proximity to the lower side surface of the reducing container and to thereby completely suck the liquids which may stagnate within the reducing container.

Finally, according to a further embodiment of the invention, reducing container 7 is suitable—with due sizing of the structure thereof—to be employed as a stand-alone unit on an appliance completely devoid of a conventional sterilisation chamber. In other words, an appliance apt to perform exclusively short treatment and sterilisation cycles exclusively within one or more self-contained reducing containers 7.

According to this further embodiment, the volume limitation of reducing container 7 over conventional autoclaves is compensated by the inexpensiveness of the same and by the speed of each cycle: it is therefore possible to provide an appliance base unit onto which a plurality of self-contained reducing containers is apt to be connected.

Examples of such solution are illustrated in FIGS. 5-10.

In particular, FIG. 5 shows an appliance base unit, equipped with devices suitable to perform sterilisation or other treatment operations, onto which two self-contained reducing containers are applicable in an upright position. In FIGS. 6 and 7 two other possible embodiments of the system of FIG. 5 are illustrated, onto which four smaller-sized reducing containers are also applicable.

FIG. 8 shows another possible system, wherein the reducing containers are connected in a substantially horizontal position; a possible mode of insertion of a handpiece into a corresponding reducing container equipped with an injection head is simultaneously shown which, after undergoing a desired treatment cycle by means of the appropriate appliance, is stored in a sterile condition in the closed reducing container.

Figure 9C:
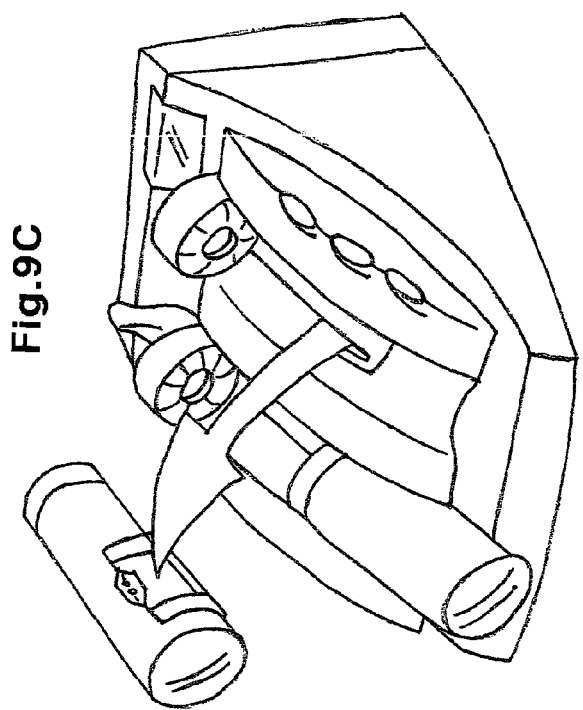
FIGS. 9A-9C are diagrammatical perspective views showing another embodiment of the invention.
Figure 9A:
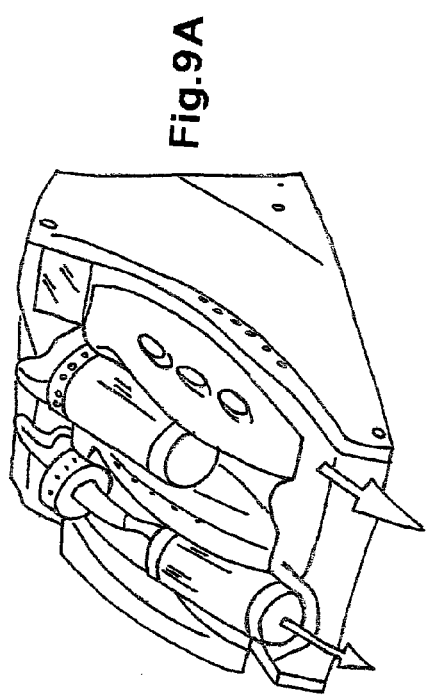
Figure 9B:
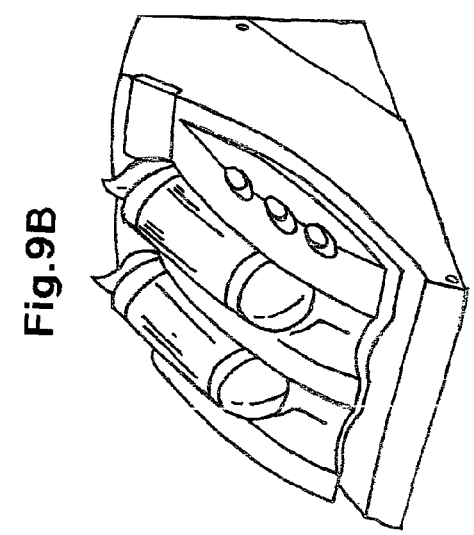

FIGS. 9A-9C show another embodiment of an appliance devoid of a conventional sterilisation chamber, onto which two reducing containers are connectable. It can be appreciated that the reducing containers can be fully removed with their respective ring nut and carrying block of the handpiece, or they can be simply disassembled to open them and remove the handpiece and the respective carrying block on the appliance. In this last case, a retaining system is provided on the base unit, so that the main body of the container is shifted, for example through a rotation and then a translation movement, and remains engaged with the base unit (so that it cannot get lost), whereas the handpiece can be removed and used by the dentist.

Figure 10:
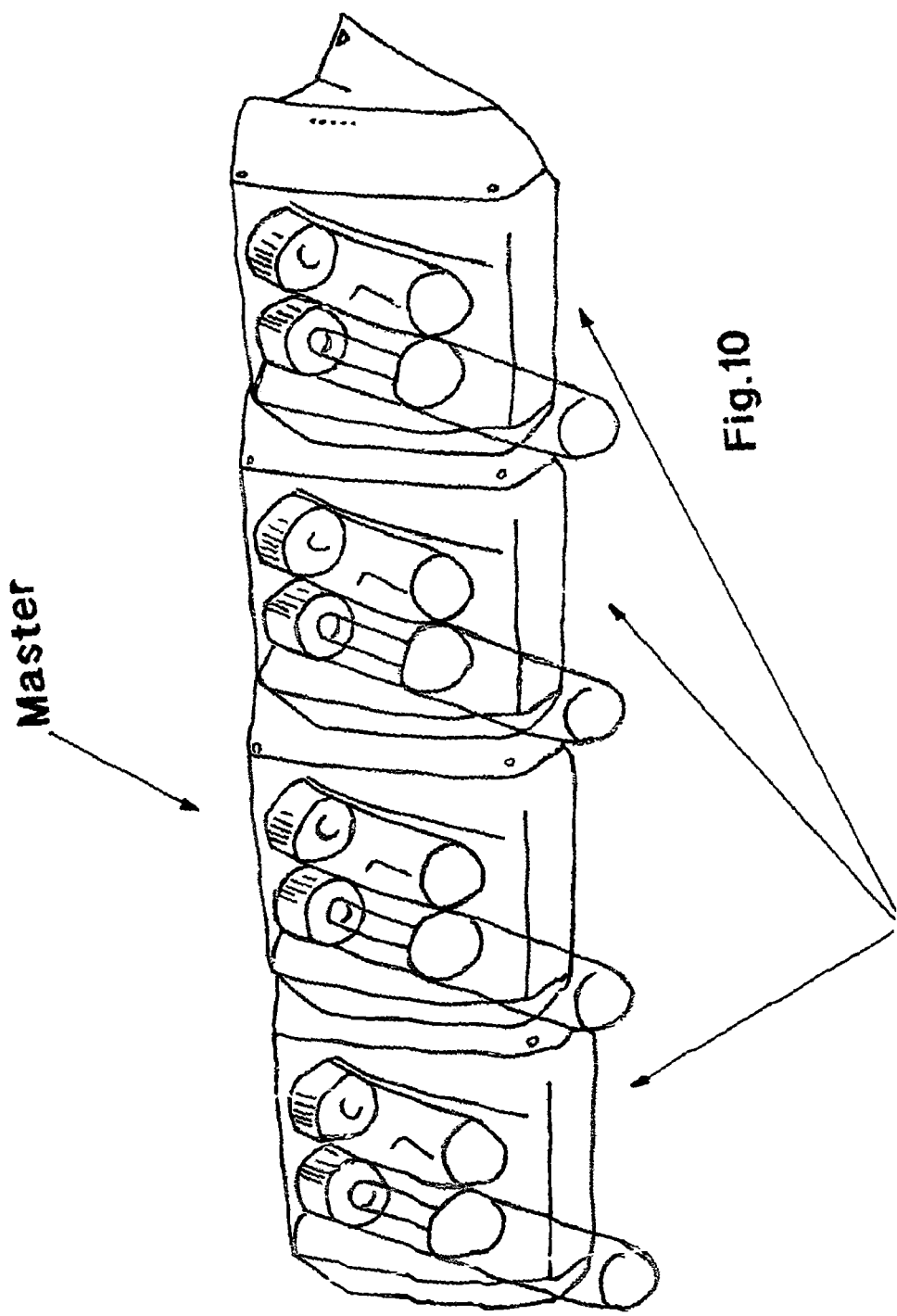
FIG. 10 is a diagrammatical perspective view which shows a modular embodiment of the invention.

Finally, FIG. 10 shows a possible modular system, wherein a master element is provided—similar to the one shown in FIG. 9A—as well as a plurality of slave elements which can be coupled with the master one. The strong point of this composition is evidently the fact of allowing widening of the system by using a single costly module—which contains the main functional devices—and a series of cheaper modules.

Figure 11:
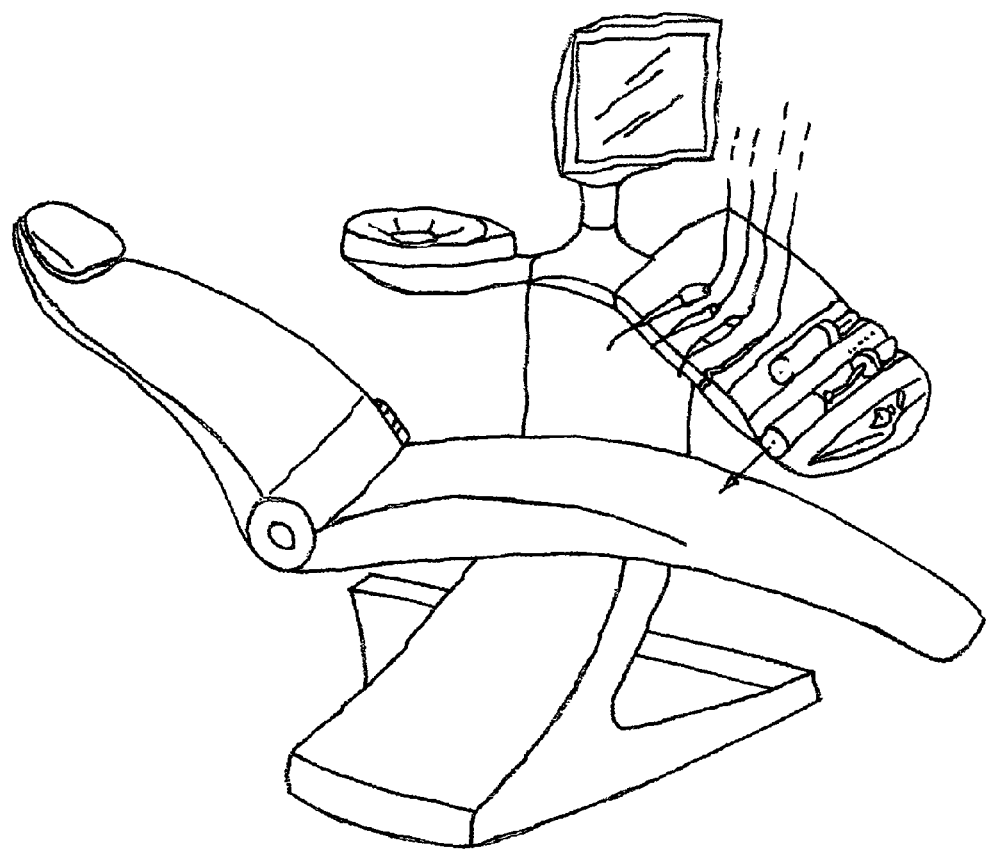
FIG. 11 is a diagrammatical perspective view which shows a treatment system according to the invention integrated in a dentist's unit.
Figure 12:
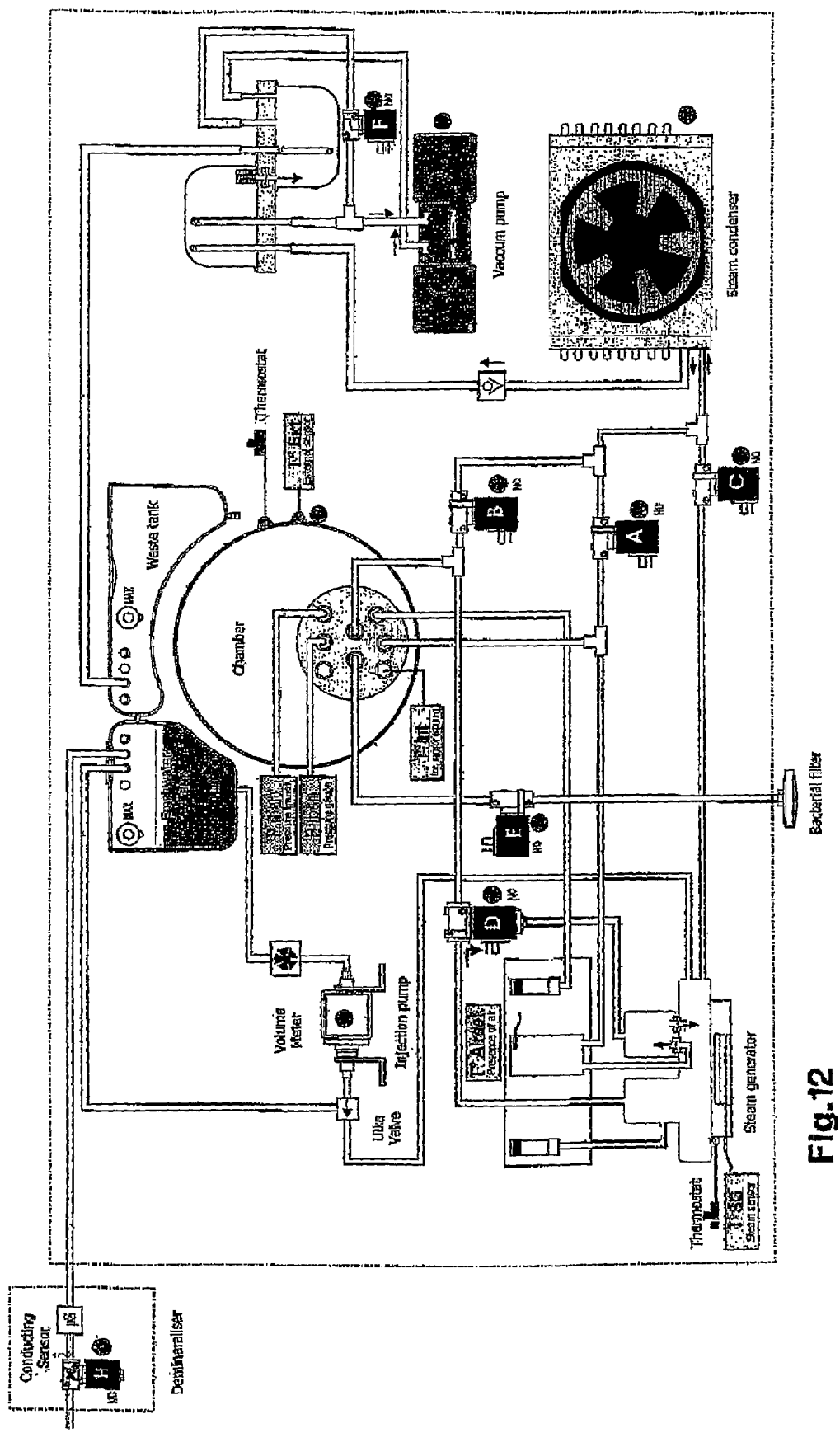
FIG. 12 is a circuit diagram of an exemplary autoclave according to the invention.

In the last analysis, the work base unit containing the functional devices (steam generator, vacuum pump, evacuation pump, and so on) can also be integrated in the same dentist's unit of a dental surgery (FIG. 11).

As can be well understood, through the improved autoclave and the small-sized self-contained container here described, it is possible to advantageously achieve the objects set forth in the preamble.

However, it is understood that the invention is not limited to the specific embodiments illustrated above, which merely represent non-limiting examples of the scope of the invention, but that a number of variants are possible, all within the reach of a skilled person in the field, without departing from the scope of the invention.

For example, although studs 5 have been shown as a quick-fitting system to fit reducing container 7 to connection body 3, many other suitable means can be used on each occasion.

Moreover, it can be envisaged that even the autoclave can be designed to house one or more self-contained reducing containers, correspondingly providing the same number of connecting and fitting partitions, which may be operated upon in order to render them inoperative when they are not in use. This technical possibility, which does not depart from the teachings offered here, can be applied at an industrial level, should it be justified by issues of economic and practical convenience.

The invention claimed is:

1. An autoclave device for sterilization of clinical instruments, comprising:
    an outer chamber having a base plate; and
    an inner chamber, the inner chamber comprising:
        a connection body or partition, the connection body or partition being integrally moulded to have at least one fitting configured for inflow and outflow of fluids, the connection body having an inner piece and an outer piece abutting two opposite sides of the base plate to form a seal; and
        a self-contained can-shaped reducing container fitted to the connection body or partition with a quick connect/disconnect fitting, the reducing container having an inner volume which is less than an interior volume of the outer chamber, the inner volume of said reducing container communicating exclusively with said at least one fitting, said reducing container being configured to be fully contained within the interior volume of said outer chamber,
    wherein sterilization occurs inside the inner chamber.

2. The autoclave device as in claim 1, wherein said reducing container is made of polymeric and/or glass material.

3. The autoclave device as in claim 1, wherein said connection body has a bayonet fitting and said reducing container has an opening equipped with a corresponding bayonet engagement device.

4. The autoclave device as in claim 1, wherein said connection body has appliance fittings to transfer work fluids through a closure arranged at a mouth end of said can-shaped reducing container.

5. The autoclave device as in claim 4, wherein said closure prevents the passage of bacterial charge.

6. The autoclave device as in claim 5, wherein said closure comprises a semi-permeable membrane.

7. The autoclave device as in claim 1, wherein said at least one fitting is configured to input and output air, sterilization fluids and cleaning/disinfecting and lubrication fluids, there being further provided at least one suction intake of cleaning and lubrication residues.

8. The autoclave device as in claim 1, wherein the inner piece and the outer piece are pack fastened via a means for fastening.

9. The autoclave device as in claim 8, wherein means for fastening comprise a series of nuts and stud bolts.

10. The autoclave device as in claim 1, wherein the inner piece and the outer piece are formed from 30% glass-filled polyetheramide.

11. The autoclave device as in claim 1, wherein the can-shaped reducing container has the inner volume being less than $2/3$ of the interior volume of the outer chamber.

12. The autoclave device as in claim 1, wherein the can-shaped reducing container is formed from glass-filled polyetheramide.

13. The autoclave device as in claim 1, wherein the can-shaped reducing container has a length of 280-300 mm and a diameter of 120-130 mm.

* * * * *